(12) United States Patent
Imai

(10) Patent No.: US 7,988,667 B2
(45) Date of Patent: Aug. 2, 2011

(54) PIERCING TOOL

(75) Inventor: Masaomi Imai, Yamanashi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/597,685

(22) PCT Filed: Apr. 16, 2008

(86) PCT No.: PCT/JP2008/057444
§ 371 (c)(1),
(2), (4) Date: Nov. 11, 2009

(87) PCT Pub. No.: WO2008/136271
PCT Pub. Date: Nov. 13, 2008

(65) Prior Publication Data
US 2010/0137799 A1    Jun. 3, 2010

(30) Foreign Application Priority Data

Apr. 27, 2007  (JP) ................. 2007-119560

(51) Int. Cl.
*A61M 5/42*  (2006.01)
(52) U.S. Cl. .............. 604/115; 604/164.04; 604/164.12; 606/167; 606/185; 128/99.1; 128/102.1; 128/876; 128/878; 128/879
(58) Field of Classification Search ............... 604/93.01, 604/115–117, 164.01, 164.04, 164.12, 263–264, 604/272, 174, 179–180; 600/573, 576, 578; 606/167, 181, 184–185, 186; 128/99.1, 900.1, 128/101.1, 102.1, 876, 878–879
See application file for complete search history.

(56) References Cited

U.S. PATENT DOCUMENTS

| | | | | |
|---|---|---|---|---|
| 2,451,183 | A | * | 10/1948 | Tantimonaco ................ 604/115 |
| 4,360,016 | A | * | 11/1982 | Sarrine ......................... 600/576 |
| 4,809,700 | A | * | 3/1989 | Castelli ........................ 600/384 |
| 6,706,000 | B2 | * | 3/2004 | Perez et al. ................... 600/583 |
| 6,743,211 | B1 | * | 6/2004 | Prausnitz et al. ............. 604/239 |
| 2002/0002344 | A1 | * | 1/2002 | Douglas et al. .............. 600/583 |
| 2002/0032415 | A1 | * | 3/2002 | Trautman et al. ............ 604/272 |
| 2007/0156064 | A1 | * | 7/2007 | Ritchart et al. .............. 600/564 |
| 2008/0027385 | A1 | * | 1/2008 | Freeman et al. ............. 604/117 |

FOREIGN PATENT DOCUMENTS

| | | |
|---|---|---|
| JP | 2002-219115 A | 8/2002 |
| JP | 2005-087519 A | 4/2005 |

OTHER PUBLICATIONS

International Search Report for PCT/JP2008/057444, completed Jul. 17, 2008.

* cited by examiner

*Primary Examiner* — Nicholas D Lucchesi
*Assistant Examiner* — Quynh-Nhu H Vu
(74) *Attorney, Agent, or Firm* — Buchanan Ingersoll & Rooney PC

(57) ABSTRACT

A piercing tool (1) can safely and reliably pierce a piercing needle (411) into a skin layer. The piercing tool (1) comprises a belt-like flexible fixing member (2) having an opening (3) formed for raising skin, and a piercing needle moving means (4) mounted on the belt-like fixing member (2) for movably holding the piercing needle (411). By moving the piercing needle moving means (4), the piercing needle (411) is moved so as to be pierced into the skin raised from the opening (3).

8 Claims, 10 Drawing Sheets

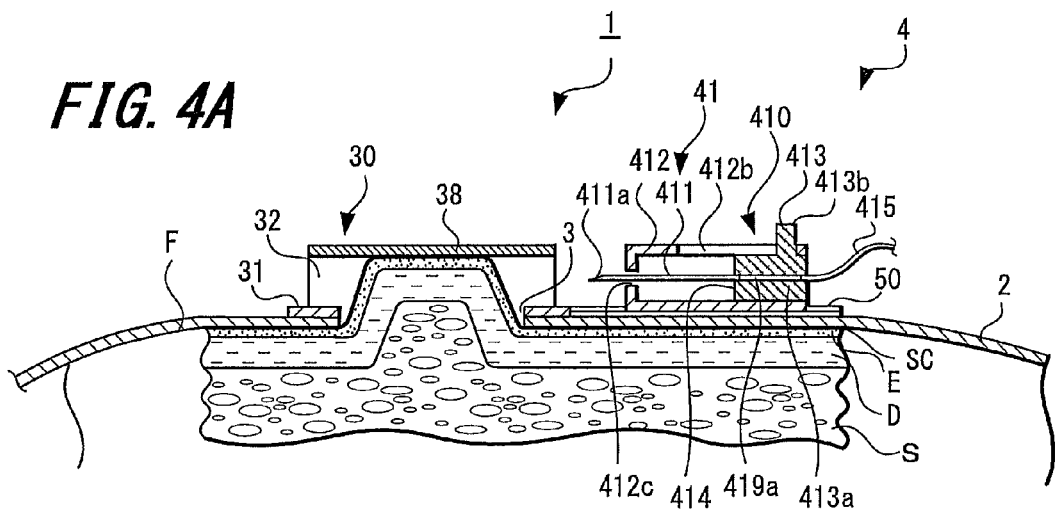
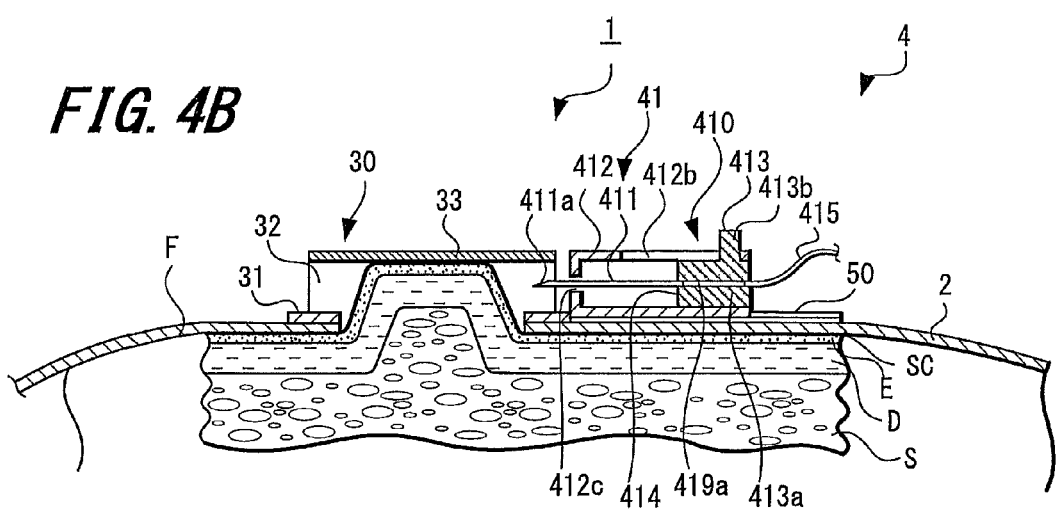
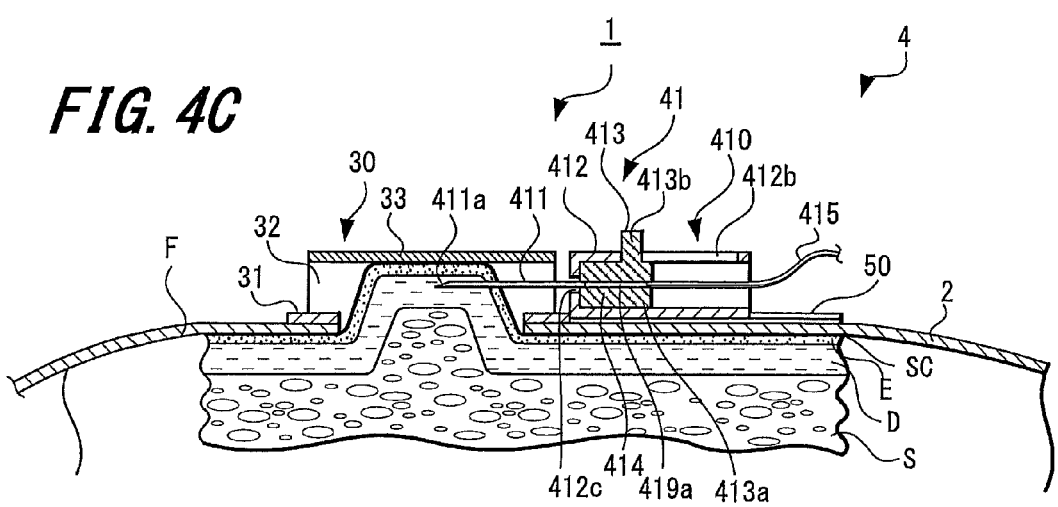

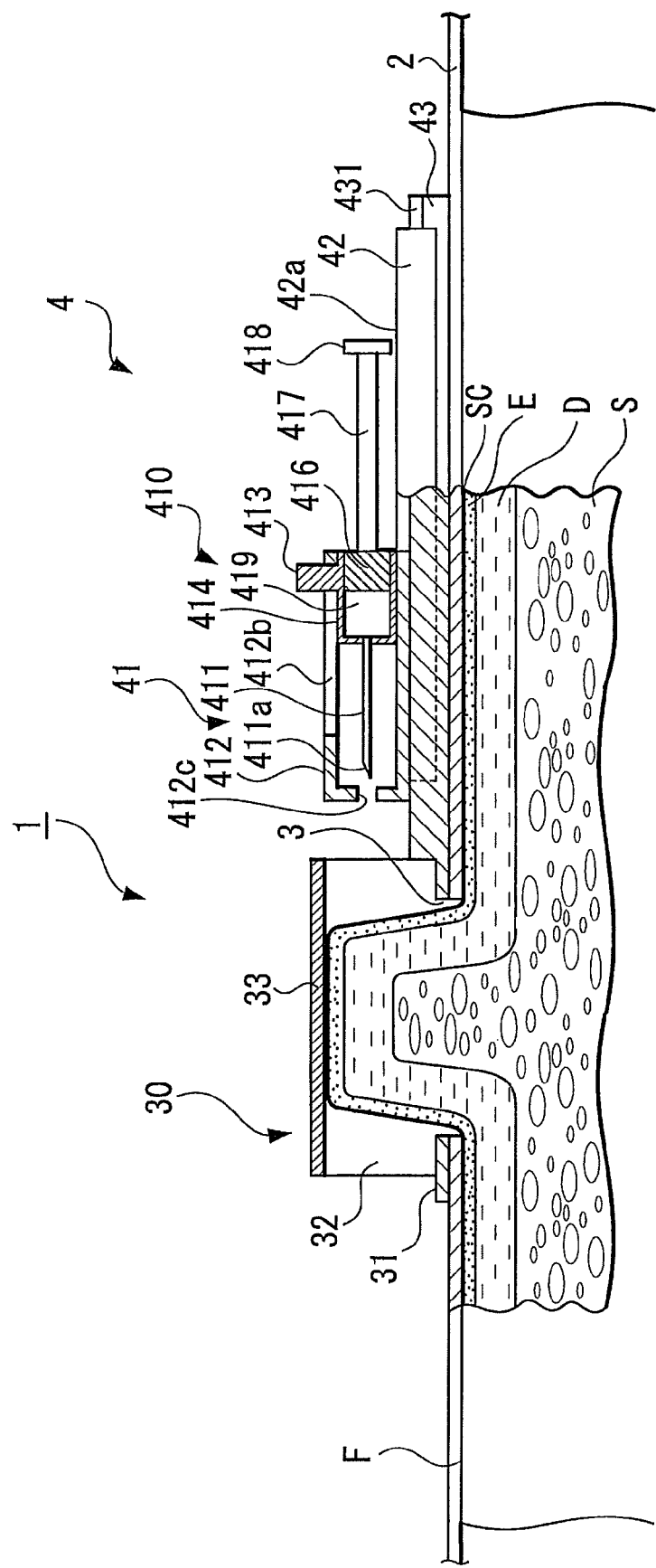

PIERCING TOOL

TECHNICAL FIELD

The present invention relates to a piercing tool, more particularly to a piercing tool for piercing a skin from the surface of the skin into a predetermined region (e.g., dermis).

BACKGROUND ART

It is known that the dermis has high density of capillary blood vessels compared to both the epidermis and the subcutaneous tissue, and has lymph vessel ends. Therefore, directly injected medical agents, in particular, tend to migrate into the blood vessels and/or the lymph vessels, and therefore the absorption speed of the medical agents into the body fluid becomes higher. Particularly, medical agents using macromolecular substance(s) such as hormone, antibody drug, cytokine and the like can be efficiently absorbed into the blood in the dermis. It is also known that the dermis is a place of efficient immunity, which makes it possible to save dose of a vaccine and to strengthen sensitization of a weak vaccine.

Further, it is known that, with respect to a man or woman grown up to some extent, the dermis exists in a certain depth from his or her body surface (i.e., from the surface of his or her stratum corneum). In other words, this fact means that, when injecting a medical agent into the dermis of an adult, it is possible to use a piercing needle having the same length (depth).

Generally, the thickness of the dermis is around 1 mm to mm (average value is 1 mm to 2 mm) in a direction perpendicular to the body surface as a reference. Further, as shown in the cross sectional view of a general skin structure of FIG. 10, the dermis is a layer of skin between an epidermis E and a subcutaneous tissue S, wherein the epidermis E includes a stratum corneum SC and has a thickness of around 0.06 mm to 0.1 mm.

Accordingly, it is difficult to accurately insert a medical agent outlet of the piercing tool (e.g., a needlepoint of the piercing needle) to the dermis between the epidermis and the subcutaneous tissue. If the needlepoint is accidentally inserted to the subcutaneous tissue or the like, the medical agent will fail to be efficiently absorbed.

In recent years, for example, attempts have been made to administer, continuously or in one shot, a medicine using the aforesaid macromolecular substance(s) into the dermis as a target, however the aforesaid problems are prominent in these attempts.

Here, there is known a hypodermic injection device in which the length of the piercing needle to be inserted into the body is defined such that the medical agent is injected into the dermis of the body (see Patent Document 1). Further, there is also known a medical solution injection device in which the depth (insertion depth) of the piercing needle to be inserted into the skin is defined as a predetermined length so that the medical agent is injected into a specific layer of the skin, wherein the piercing needle is inserted into the skin in a direction perpendicular to the body surface (see Patent Document 2).

[Patent Document 1] Japanese Laid-Open Patent Application Publication No. 2001-137343

[Patent Document 1] Japanese Laid-Open Patent Application Publication No. 2005-87519

DISCLOSURE OF THE INVENTION

However, in the aforesaid devices, a configuration is employed in which a piercing needle is inserted into the skin in a direction perpendicular to the body surface. With such a configuration, when attempting to pierce the piercing needle into the skin, there is a possibility that the piercing needle might fail to be pierced into the skin because the whole skin is elastically recessed, or the needlepoint (i.e., the medical agent outlet) of the piercing needle might fail to reach the dermis even if the piercing needle is pierced into the skin.

Further, when the piercing needle is inserted in a direction perpendicular to the dermis, there is a concern that the depth of the piercing needle in the dermis (i.e., insertion depth) may shorten, or the piercing needle may drop out from the dermis during injection of a medical agent when, for example, subjected to some kind of external impact or the like.

Further, when using such devices, since the distance between the insertion opening of the piercing needle formed on the surface of the dermis (i.e., boundary portion of epidermis and dermis) and the medical agent outlet at the tip end of the piercing needle becomes short, there is a concern that the medical agent injected from the medical agent outlet into the dermis may leak from the insertion opening to the outside of the dermis (i.e., to the epidermis).

Further, when deforming the skin to insert the piercing needle into the skin, there is a concern that the piercing needle may not be pierced into the correct region of the skin if the member for deforming the skin is not stably fixed to the skin.

In view of the aforesaid problems, it is an object of the present invention to provide a piercing tool capable of reliably piercing a piercing needle into a predetermined region of the skin.

The above object is achieved by the following aspects (1) to (4) of the present invention.

(1) A piercing tool for piercing a piercing needle into a skin, comprising: a belt-like flexible fixing member having an opening formed for raising the skin; and a piercing needle moving means mounted on the belt-like fixing member for movably holding the piercing needle, wherein, by moving the piercing needle moving means, the piercing needle is moved so as to be pierced into the skin raised from the opening.

(2) The piercing tool according to aspect (1), wherein the belt-like fixing member is provided with an adjusting means for adjusting the fixing position of the piercing tool when attaching the piercing tool to a body.

(3) The piercing tool according to aspect (1) or (2), wherein the opening of the belt-like fixing member is provided with a regulating member for regulating the condition of the skin raised from the opening.

(4) The piercing tool according to aspect (1), wherein the piercing needle moving means is moved in a direction perpendicular to the longitudinal direction of the belt-like fixing member.

According to the present invention, it is possible to pierce the piercing needle into the skin in a state where the piercing tool is reliably fixed to the body, so that the needlepoint (the medical agent outlet) can reliably reach the predetermined region (e.g., the dermis).

BRIEF DESCRIPTION OF DRAWINGS

FIG. 4 illustrates views (cross sectional views) for explaining how to use the piercing tool of FIG. 1.

FIG. 6 is a cross sectional view taken along line A-A of FIG. 5.

BEST MODES FOR CARRYING OUT THE INVENTION

Best embodiments of the piercing tool according to the present invention will be described below with reference to the attached drawings. However it should be noted that the present invention is not limited to these embodiments.

Figure 1:
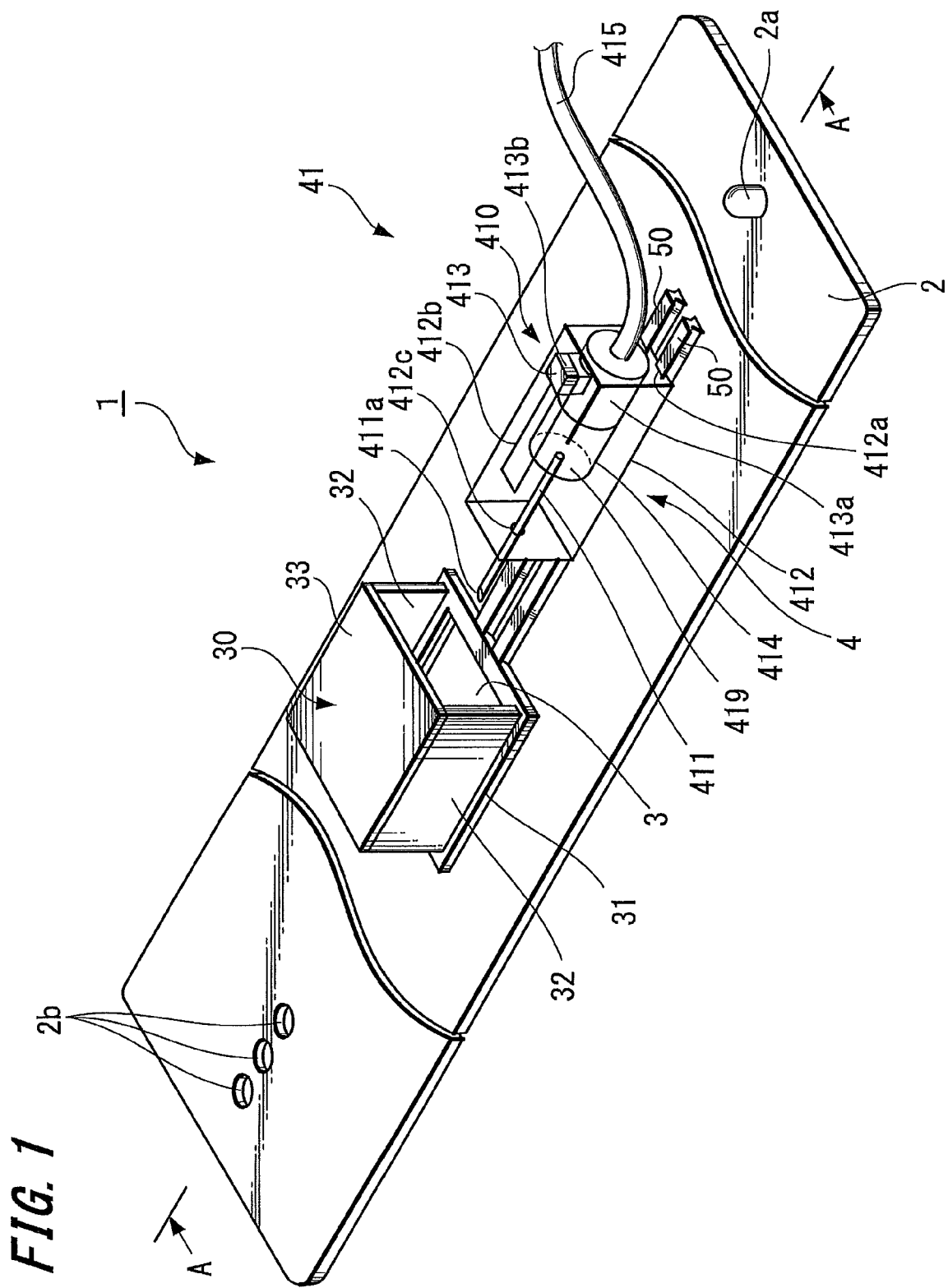
FIG. 1 is a perspective view showing a piercing tool according to a first embodiment of the present invention.
Figure 2:
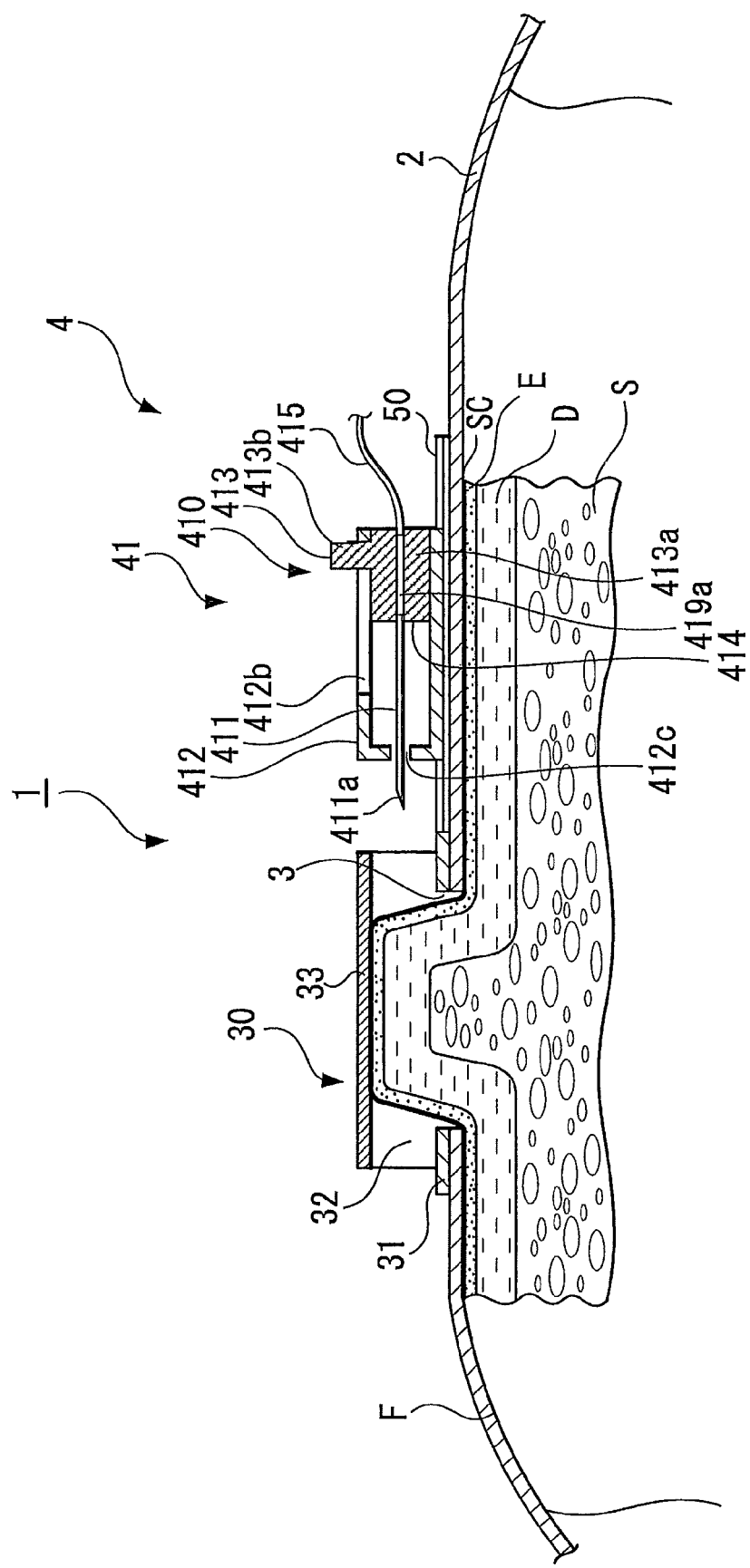
FIG. 2 is a cross sectional view taken along line A-A of FIG. 1.
Figure 3:
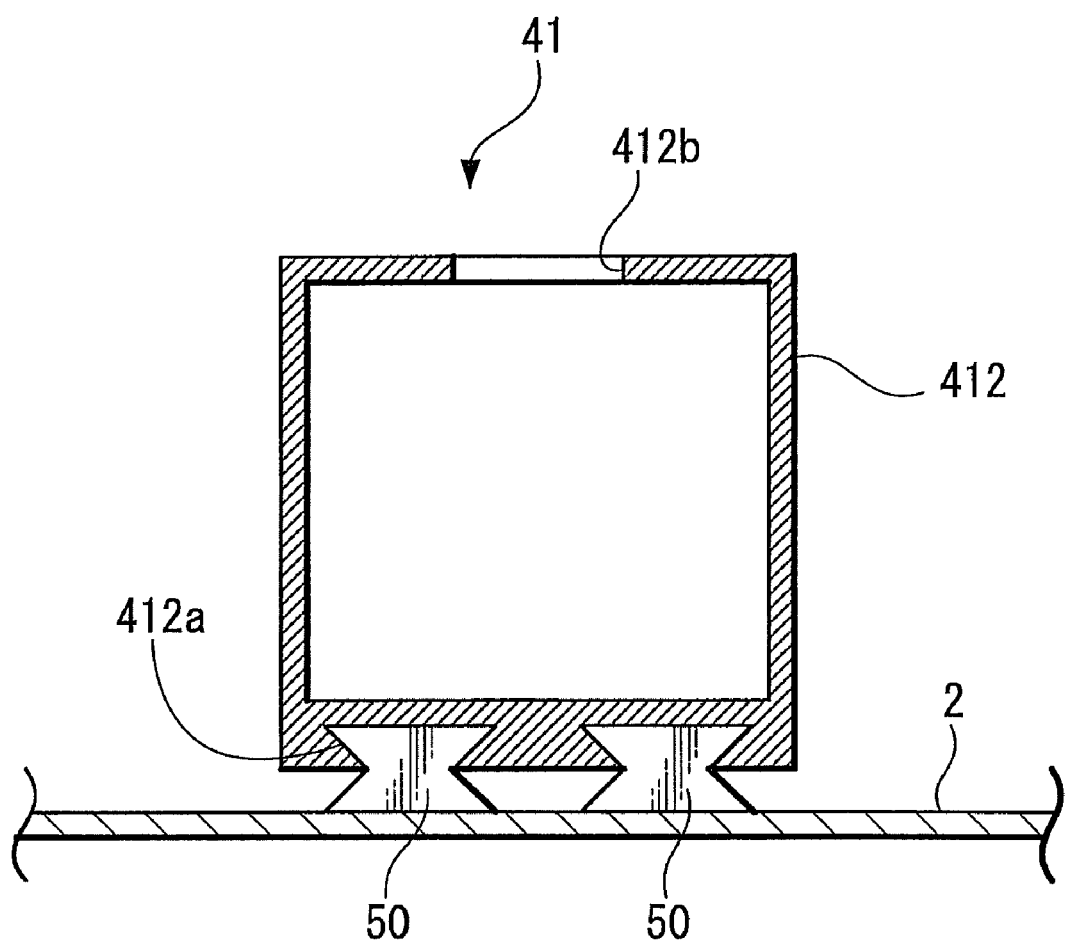
FIG. 3 is a cross sectional view for explaining an engaging state between an outer tube and rails of FIG. 1.

FIG. 1 is a perspective view showing a piercing tool according to a first embodiment of the present invention. FIG. 2 is a cross sectional view taken along line A-A of FIG. 1 when the piercing tool is fixed to the body of a user. FIG. 3 is a cross sectional view for explaining an engaging state between an outer tube and rails of FIG. 1. FIG. 4 illustrates views (cross sectional views) for explaining how to use the piercing tool of FIG. 1.

Note that, in the following description, the right side of FIGS. 2 and 4 is referred to as "proximal end", and the left side is referred to as "distal end".

As shown in FIGS. 1 and 2, a piercing tool 1, which is a first embodiment of the piercing tool of the present invention, includes a belt-like fixing member 2 for fixing the piercing tool to the body of a user, an opening portion having an opening 3 for upwardly raising skin, a piercing needle moving means 4 for movably holding a piercing needle 411, and the like.

The belt 2 is a band-like component formed of a flexible member. Examples of the constituent material of the belt 2 include, for example, synthetic resins and rubbers such as soft polymer like soft polyurethane, rubber elastic elastomer, and the like. A pin-like engaging projection 2a is formed near one end of the belt 2. A plurality of engaging holes 2b are formed near the other end of the belt 2. The plurality of engaging holes 2b are arranged at an equal interval along a central line in the longitudinal direction of the belt 2.

The user of the piercing tool fixes the piercing tool 1 on his or her body by wrapping the belt 2 around a predetermined portion of the body, and engaging the engaging projection 2a to a particular engaging hole 2b in a state where the skin is raised from the opening 3. At this time, the fixing position of the piercing tool 1 can be adjusted to a position best suited to the body by making the engaging holes 2b, into which the engaging projection 2a is to be inserted, displaced from each other. In other words, the engaging projection 2a and the engaging holes 2b constitute an adjusting means. Further, since the belt 2 is flexible, the piercing tool can be mounted without creating a gap between the piercing tool and the skin.

As shown in FIG. 2, the piercing tool 1 is closely fixed to a body surface F of the predetermined portion of the body by the belt 2. Incidentally, stratum corneum SC, epidermis E including the stratum corneum SC, dermis D and subcutaneous tissue S are layered under the body surface F.

The opening portion for raising skin is formed in a central portion of the belt 2. The rectangular shaped opening 3 is formed in the opening portion. In the present embodiment, the opening 3 is formed so that the longitudinal direction thereof becomes parallel with the longitudinal direction of the belt 2. Note that the shape of the opening is not limited to the shape described in the present embodiment.

A regulating member 30 for adjusting the condition of the skin raised from the opening is provided around the opening 3. The regulating member 30 includes a supporting table 31 provided around the opening 3, two side plates 32 arranged on the supporting table 31 along the longitudinal direction of the opening 3, and a top plate 33 provided above the two side plates 32 so as to face the opening 3. Owing to the top plate 33, the height of the skin raised from the opening 3 is regulated to a predetermined height. The top plate 33 is formed in a flat plate shape in the present embodiment, however top plate 33 may also be formed so that a surface thereof facing the opening 3 is arc-shaped in the cross section of the top plate 33 in a direction perpendicular to the moving direction of the piercing needle 411, and therefore the raised skin is deformed into an arc shape.

Further, the side plates may be arranged along a direction perpendicular to the longitudinal direction of the opening. In such a case, an insertion hole should be formed in the side plate facing the piercing needle 411 to allow the piercing needle to be inserted therein. Incidentally, although the regulating member for regulating the height of the raised skin is provided in the present embodiment, the regulating member does not have to be provided when the piercing needle is pierced under visual observation.

The piercing needle moving means 4 is provided near the central portion of the belt 2 so as to be adjacent to the opening 3. The piercing needle moving means 4 includes a guide portion configured by two rails 50 disposed on the surface of the belt 2 along the longitudinal direction of the belt 2, and an injector 41 having the piercing needle 411. Incidentally, the guide portion of the piercing needle moving means 4 may either be fixed to the belt 2, or be detachable from the belt 2, instead of being fixed to the belt 2, in the case where the rails 50 of the guide portion are rigidly-bonded to or integrally formed with the supporting table 31 of the regulating member 30.

The injector 41 includes the piercing needle 411, a needle holding member 410 for holding the piercing needle 411, and an outer tube 412 for containing the needle holding member 410 and part of the piercing needle 411.

The outer tube 412 is formed in a rectangle shape. As shown in FIG. 3, engaging recesses 412a are formed in a surface of the outer tube 412 opposing the belt 2, the shape of the engaging recesses 412a conforming the shape of the rails 50. By engaging the engaging recesses 412a with the rails 50, the outer tube 412 can be slid along the rails 50 in the longitudinal direction of the belt 2. Further, a guiding hole 412b is formed in a central portion of the upper surface of the outer tube 412 along the longitudinal direction of the belt 2.

Examples of the constituent material of the outer tube 412 include various resins such as polyvinyl chloride, polyethylene, polypropylene and the like. Incidentally, in order to ensure the visibility of the inside, the outer tube 412 is preferably formed of a substantially transparent material.

Note that, the guide portion is not limited to the configuration of the present embodiment, but may have a configuration, for example, in which two flexible fastener-like members are provided in parallel on the belt 2, engaging teeth are formed in a surface of each of the fastener-like members facing the bottom surface of the outer tube 412, and an engaging portion is provided on the bottom surface of the outer tube 412 so that the engaging portion can be engaged with and slid along the fastener-like members.

The needle holding member 410 has a cylindrical shaped inner tube 414, and the piercing needle 411 is mounted on a side surface of the inner tube 414 on the opening portion side so that the piercing needle 411 extends along the longitudinal direction of the belt 2. The piercing needle 411 is mounted in a state where the needlepoint 411a protrudes to the outside from an insertion hole 412c formed in the outer tube 412. Incidentally, a protective cover such as a cap may be mounted on the protruded needlepoint 411a.

The outer diameter of the piercing needle 411 may differ slightly, depending on the intended use of the piercing tool 1, preferably within a range of 0.05-2 mm, more preferably within a range of 0.1-1.5 mm.

Examples of the constituent material of the piercing needle 411 include metallic material such as stainless steel, aluminum, aluminum alloy, titanium, titanium alloy and the like. Further, the piercing needle 411 is manufactured by, for example, plastic forming processes.

A gripping portion 413 is formed on a side of the inner tube 414 opposite to the side of the opening portion. The gripping portion 413 includes a cylindrical shaped base 413a, and a grip 413b integrated with the base 413a. The grip 413b is configured so as to protrude from the guiding hole 412b formed in the outer tube 412.

A flow passage 419a is formed inside the inner tube 414. A tube 415 is connected to the base 413a for injecting a medical solution or the like into the flow passage 419a. Although the tube 415 is fixed to the base 413a in the present embodiment, the present invention also includes a configuration in which a fitting portion for fitting the tube is formed on the base 413a, and the tube is detachably fitted to the base 413a. Incidentally, the present invention also includes a configuration in which a connection port is formed in the base, and the medical solution or the like is directly injected from a syringe or a catheter connector without using a tube.

Examples of the liquid include, for example, injectable medicines, and medical solutions using macromolecular substance(s) such as hormone, antibody drug, cytokine, vaccine and the like.

The user of the piercing tool 1 can move the piercing needle 411 by gripping and operating the grip 413b protruded from the guiding hole 412b with fingers.

Next, usage (function) of the piercing tool 1 according to the first embodiment will be described below.

First, as shown in FIG. 4(a), the piercing tool is wrapped around a proper portion of a wrist, a forearm, an upper arm or a leg of the user, so that the piercing tool is fixed to a predetermined position of the body surface F. Particularly, the wrapping position should be adjusted so that soft site of the skin is located in the opening portion. At this time, the piercing tool 1 is fixed to the body surface F by engaging the engaging projection 2a with one of the engaging holes 2b. Specifically, when fixing the piercing tool 1, due to the pressing force of the belt to the skin, the skin around the opening 3 is pressed while the skin facing the opening 3 is raised upwardly. That is, the epidermis E including the stratum corneum SC, the dermis D and the subcutaneous tissue S are respectively pressed upwardly, so that the skin is raised from the opening 3 in a direction perpendicular to the body surface F.

Herein, since the position of the top plate 33 of the regulating member 30 is set to a predetermined height, the height of the dermis D of the raised skin and the height of the piercing needle 411 mounted on the piercing needle moving means 4 are substantially the same.

Next, as shown in FIG. 4(b), the outer tube 412 is slid along the rails 50, so that the injector 41 is slid toward the distal end. That is, the outer tube 412 is moved close to the side surface of the raised skin, so that the needlepoint 411a of the piercing needle 411 is moved close to the side surface of the raised skin. Incidentally, in the case where the protective cover is attached to the needlepoint portion of the piercing needle 411, the protective cover should be previously detached.

Next, after visually confirming that the skin raised from the opening portion has been raised to a position sufficiently higher than the position of the needlepoint 411a of the piercing needle 411, the grip 413a which is integrated with the inner tube 414 of the needle holding member 410 is gripped and slid toward the distal end along the guiding hole 412b formed in the outer tube 412. Thereby the inner tube 414 is slid inside the outer tube 412, so that the piercing needle 411 provided to the inner tube 414 is pierced into the raised skin. That is, as shown in FIG. 4(c), the needlepoint 411a of the piercing needle 411 is penetrated through the epidermis E including the stratum corneum SC, and is inserted into the dermis D substantially in parallel to the dermis D.

Next, the liquid supplied from the tube 415 connected to the base 413a of the needle holding member 410 and filled in the flow passage 419a and the piercing needle 411 is injected into the dermis D through the needlepoint 411a of the piercing needle 411.

After the liquid is injected into the dermis D, the outer tube 412 is slid toward the proximal end along the rails 50 so that the piercing needle 411 is pulled out from the raised skin, and finally the engaging projection 2a of the belt 2 is disengaged from the engaging holes 2c so that the piercing tool 1 is detached from the body surface F.

With the piercing tool according to the present embodiment, the piercing needle 411 is pierced into the skin in the state where the piercing tool 1 is reliably fixed to the body by the belt 2, so that the needlepoint 411a can reliably reach the predetermined region. Consequently, the medical solution or the like can be reliably injected into the predetermined region.

As another embodiment of the piercing tool, a cutout is formed in a direction perpendicular to the longitudinal direction of the guiding hole 412b of the outer tube 412, and the grip 413b is engaged with the cutout. At this time, a coil spring is provided between a side surface of the inner tube 414 opposite to the side where the piercing needle 411 is mounted and the inner wall of the outer tube 412, so that a biasing force from the coil spring may be constantly applied to the inner tube 414. With such a configuration, by gripping the grip 413b to release the engagement with the guiding hole 412b, the inner tube 414 is moved in the longitudinal direction of the belt owing to the biasing force of the coil spring applied to the inner tube 414, and thereby the piercing needle 411 can be pierced into the skin raised from the opening.

Further, after the medical solution is injected, the grip 413 is gripped to move the guiding hole 412b against the biasing force of the coil spring so as to engage the grip with the cutout again, and thereby the piercing tool can be used again. Incidentally, the biasing means and the engaging means may have other configurations as long as they can apply the biasing force to the inner tube 412.

Figure 5:
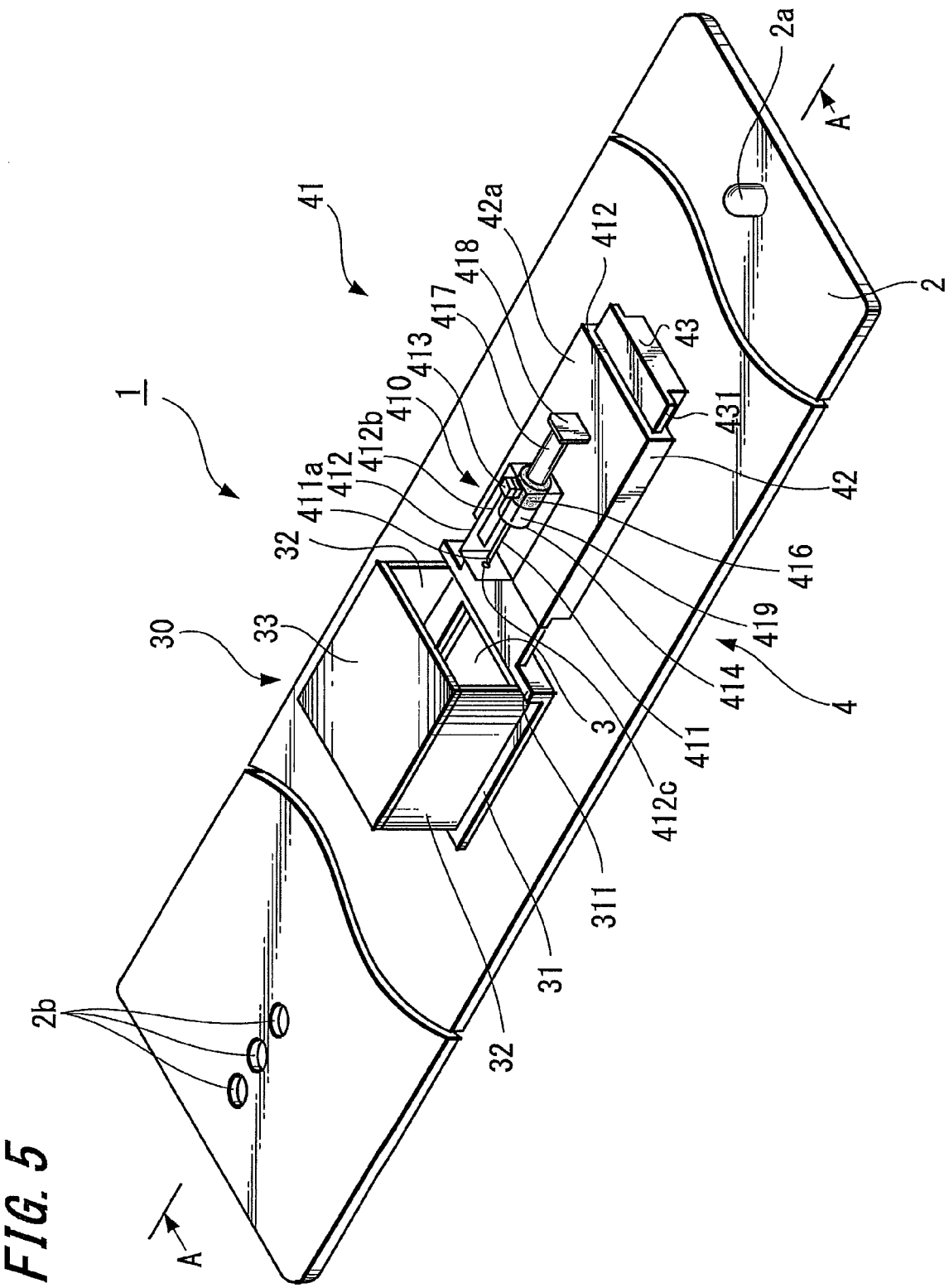
FIG. 5 is a perspective view showing a piercing tool according to a second embodiment of the present invention.

FIG. 5 is a perspective view showing a piercing tool according to a second embodiment of the present invention. FIG. 6 is a cross sectional view taken along line A-A of FIG. 5 when the piercing tool is fixed to the body. FIG. 7 illustrates views (cross sectional views) for explaining how to use the piercing tool of FIG. 5. Note that, in the following description, the right side of FIGS. 6 and 7 is referred to as "proximal end", and the left side is referred to as "distal end".

As shown in FIGS. 5 and 6, a piercing tool 1, which is a second embodiment of the piercing tool of the present invention, includes a belt-like fixing member 2 for fixing the piercing tool to the body of a user, an opening portion having an opening 3 for upwardly raising skin, a piercing needle moving means 4 for movably holding a piercing needle 411, and the like.

The belt 2 has the same configuration as that of the piercing tool according to the first embodiment.

The opening portion for raising skin is formed in a central portion of the belt 2. The rectangular shaped opening is formed in the opening portion, and the opening 3 is formed so that the longitudinal direction thereof becomes parallel with the longitudinal direction of the belt 2. Note that the shape of the opening in not limited to the shape described in the present embodiment.

A regulating member 30 for adjusting the condition of the skin raised from the opening is provided around the opening 3. The regulating member 30 has the same configuration as that of the regulating member of the first embodiment.

The piercing needle moving means 4 is provided near the central portion of the belt 2 so as to be adjacent to the opening 3. The piercing needle moving means 4 includes an injector 41 to which the piercing needle 411 is attached, a mounting member 42 for mounting and fixing the injector 41, and a supporting member 43 for movably supporting the mounting member 42.

A side piece 311 continuing from the upper face and protruding upwardly is arranged on one side of a supporting table 31 provided around the opening 3. The side piece 311 is connected with the supporting member 43 of the piercing needle moving means 4.

The injector 41 includes the piercing needle 411, an outer tube 412, an inner tube 414 slidable inside the outer tube 412, a gasket 416 slidable inside the inner tube 414, a plunger 417 for moving the gasket 416, and a flange 418 provided at an end of the plunger 417.

The outer tube 412 has a bottomed tubular shape, and is mounted and fixed to the mounting member 42 by an adhesive or the like. Further, an insertion hole 412c for allowing the piercing needle 411 to be inserted therethrough is formed near the center of the bottom of the outer tube 412.

The inner tube 414 has a bottomed tubular shape. Further, the piercing needle 411 is attached near the center of the bottom of the inner tube 414. A gripping portion 413 is integrally formed with the upper portion of the inner tube 414. The gripping portion 413 is configured so as to protrude from a guiding hole 412b formed in the outer tube 412.

The piercing needle 411 is arranged so that the needlepoint 411a does not protrude to the outside from the insertion hole 412c formed in the outer tube 412. That is, the piercing needle 411 is disposed with respect to the outer tube 412 in a manner in which the needlepoint 411a of the piercing needle 411 is located near the insertion hole 412c but on the inner side of the bottom surface of the outer tube 412 where the insertion hole 412c is formed.

With such a configuration, the needlepoint 411a of the piercing needle 411 can be protected without providing the protective cover or the like. Consequently, the needlepoint 411a of the piercing needle 411 can be prevented from being touched by fingers of the user, the fingers of the user can be protected from being accidentally pierced by the piercing needle 411, and the piercing needle 411 can be maintained in clean state. Further, since the piercing needle 411 is not subjected to external impact force directly, the piercing needle 411 can be prevented from being deformed due to impact.

The outer diameter of the piercing needle 411 may differ slightly, depending on the intended use of the piercing tool 1, preferably within a range of 0.05-2 mm, more preferably within a range of 0.1-1.5 mm.

Examples of the constituent material of the piercing needle 411 include metallic material such as stainless steel, aluminum, aluminum alloy, titanium, titanium alloy and the like. Further, the piercing needle 411 is manufactured by, for example, plastic forming processes.

By gripping and operating the gripping portion 413, the inner tube 414 can be slid inside the outer tube 412 along the longitudinal direction of the inner tube 414. Further, when sliding the inner tube 414, the piercing needle 411 fixed to the inner tube 414 is taken in and out from the outer tube 412 through the insertion hole 412c.

Examples of the constituent material of the outer tube 412 and the inner tube 414 include various resins such as polyvinyl chloride, polyethylene, polypropylene and the like. Incidentally, in order to ensure the visibility of the inside, the outer tube 412 and the inner tube 414 are preferably formed of a substantially transparent material.

The gasket 416 formed of an elastic material is housed in the inner tube 414.

The constituent material for the gasket 416 is not particularly limited. Examples of the material of the gasket 416 include elastic materials, for example, various rubber materials such as natural rubber and silicone rubber, various thermoplastic elastomers such as polyurethane elastomer, styrene elastomer and the like, and a mixture of the aforesaid materials.

A liquid chamber 419 is formed inside a space surrounded by the gasket 416 and the inner tube 414, and a liquid is liquid-tightly housed in the liquid chamber 419 previously.

Examples of the liquid include injectable therapeutic or diagnostic agent such as a medical agent using macromolecular substance(s) such as hormone, antibody drug, cytokine, vaccine and the like.

The plunger 417 for moving the gasket 416 inside the inner tube 414 along the longitudinal direction is connected to the gasket 416.

The plate-like flange 418 is integrally formed with the proximal end of the plunger 417. The plunger 417 is operated by pressing the flange 418 with a finger or the like.

The mounting member 42 is formed in a rectangular plate shape, and engaging portions 421, 421 are provided in the both side faces of the long side of the mounting member 42. The engaging portions 421, 421 are engaged with engaging projections 431, 431 as described later of the supporting member 43, so that the engaging projections 431, 431 can be slid relative to the engaging portions 421, 421. Further, the outer tube 412 of the injector 41 is fixed to an upper portion 42a of the mounting member 42.

The supporting member 43 is formed in a rectangular plate shape whose thickness is greater than that of the mounting member 42. An end of the supporting member 43 on the side of the distal end is connected to the side piece 311 of the supporting table 31. A lower portion 43b of the supporting member 43 is provided with a bonding means such as an adhesive so as to be fixed to the upper surface of the belt 2, as shown in FIG. 6. Incidentally, the present invention also includes a configuration in which the side piece 311 and the supporting member 43 are rigidly-bonded with each other or integrally formed with each other, and the supporting member 43 can be detached from the belt 2, instead of being fixed to the belt 2.

The engaging projections 431, 431 are provided in the both side faces of the long side of the supporting member 43. The engaging portions 421, 421 of the mounting member 42 are slidably engaged with the engaging projections 431, 431, and thereby the mounting member 42 is slidably supported by the supporting member 43. In other words, in the present embodiment, a guide portion is configured by the mounting member 42 and the supporting member 43.

Examples of the constituent material of the mounting member 42 and the supporting member 43 include, for example, various synthetic resins having proper strength such as acrylic resin, ABS resin and the like. However, material of the mounting member 42 and the supporting member 43 is not limited to the aforesaid synthetic resins, but may include metal such as aluminum alloy and the like.

In the present embodiment, the piercing needle moving means 4 is provided with the injector 41, and the piercing needle 411 is attached to the injector, however the present invention is not limited to such a configuration. For example, the present invention also include a configuration in which one end of a tube is connected to a side of the inner tube 414 opposite to the side where the piercing needle 411 is attached, and an injector such as liquid-feeding pump or the like is connected to the other end of the tube.

Figure 8:
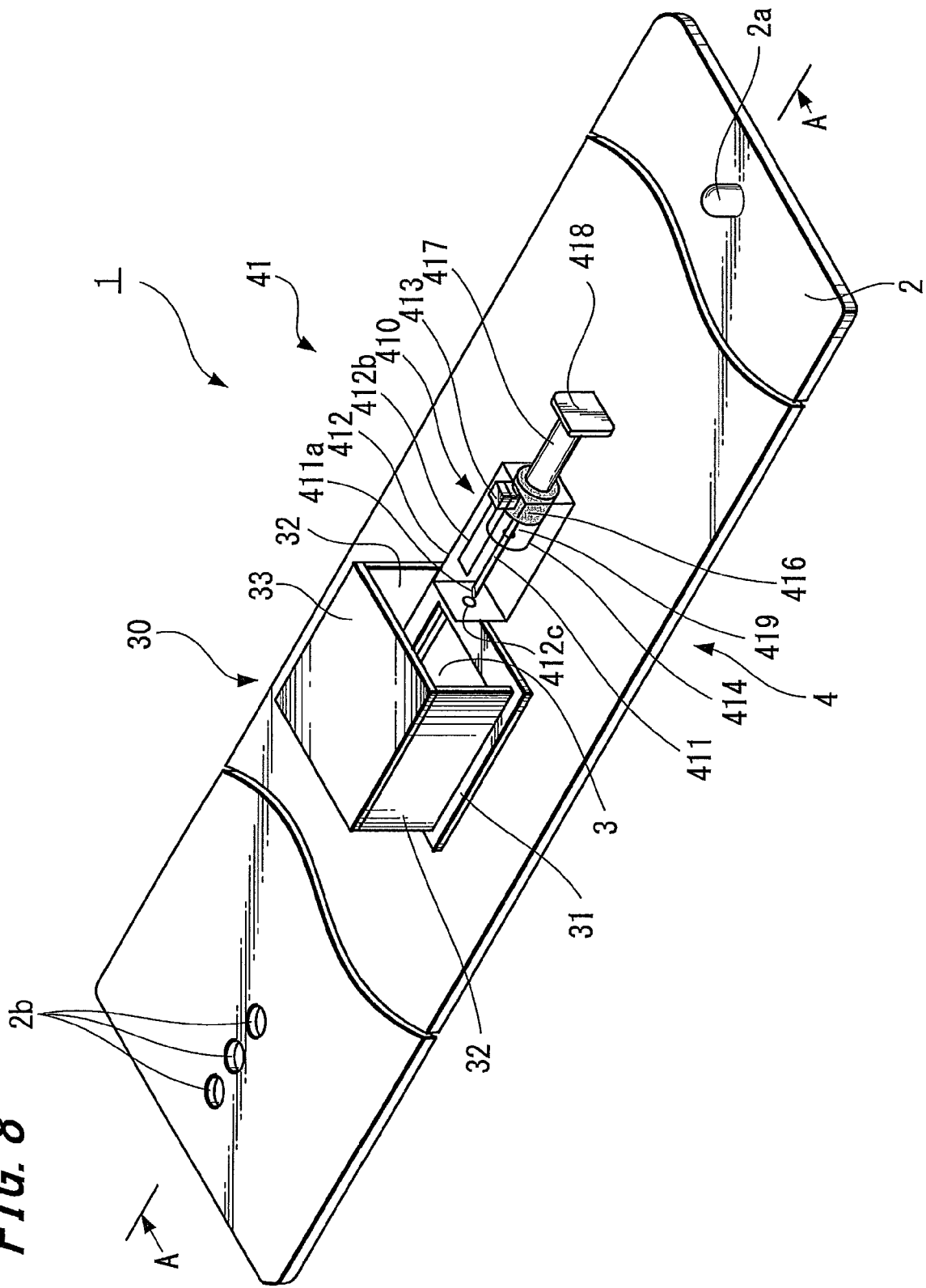
FIG. 8 is a perspective view showing a piercing tool according to a modification of the second embodiment of the present invention.

Further, as other embodiments of the piercing tool, the present invention also includes a configuration in which, as shown in FIG. 8, the injector 41 is directly mounted on the belt 2 without employing the guide portion such as the rails and the mounting member. In such a configuration, the bottom face of the outer tube 412 is adhered and fixed to the upper surface of the belt 2 by an adhesive or the like. Incidentally, the position where the outer tube 412 is fixed to the belt should be determined considering the length of the piercing needle, the moving distance of the piercing needle and the like.

Further, the present invention also includes a configuration in which the piercing needle moving means 4 and the regulating member 30 are mounted on an inflexible rigid plate-like member, and the plate-like member is fixed onto the belt 2. In such a configuration, the plate-like member is formed with an opening corresponding to the opening 3. With such a configuration, it is possible to accurately pierce the piercing needle 411 into the dermis and inject the medical solution into the dermis.

Next, usage (function) of the piercing tool 2 according to the second embodiment will be described below.

Figure 7A:
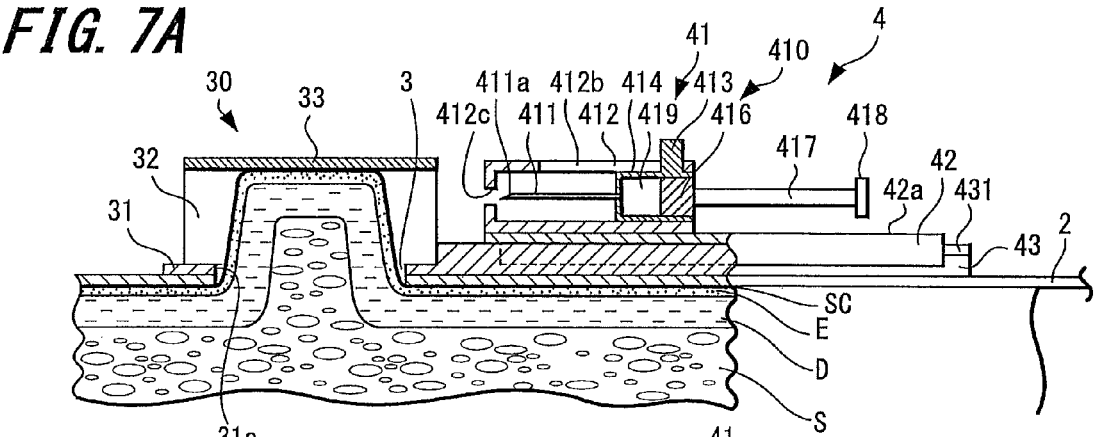
FIG. 7 illustrates views (cross sectional views) for explaining how to use the piercing tool of FIG. 5.

First, as shown in FIG. 7(a), the piercing tool is wrapped around a proper portion of a wrist, a forearm, an upper arm or a leg of the user, so that the piercing tool is fixed to a predetermined position of the body surface F. Particularly, the wrapping position should be adjusted so that soft site of the skin is located in the opening portion. The piercing tool 1 is fixed to the predetermined position of the body surface F by engaging the engaging projection 2a with one of the engaging holes 2b of the belt 2. At this time, the engaging projection 2a is engaged with one of the engaging holes 2b of the belt 2, and thereby the piercing tool 1 is fixed to the body surface F. When fixing the piercing tool 1, the skin is raised upwardly due to the pressing force of the belt to the skin. That is, the epidermis E including the stratum corneum SC, the dermis D, the subcutaneous tissue S are respectively pressed upwardly, so that the skin is raised from the opening 3 in a direction perpendicular to the body surface F.

Herein, since the position of the top plate 33 of the regulating member 30 is set to a predetermined height, the height of the dermis D of the raised skin and the height of the piercing needle 411 mounted on the piercing needle moving means 4 are substantially the same.

Next, the mounting member 42, to which the injector 41 is fixed, is slid toward the distal end. That is, the bottom surface of the outer tube 412 is moved close to the side surface of the raised skin, so that the needlepoint 411a of the piercing needle 411 is moved close to the side surface of the raised skin.

Figure 7B:
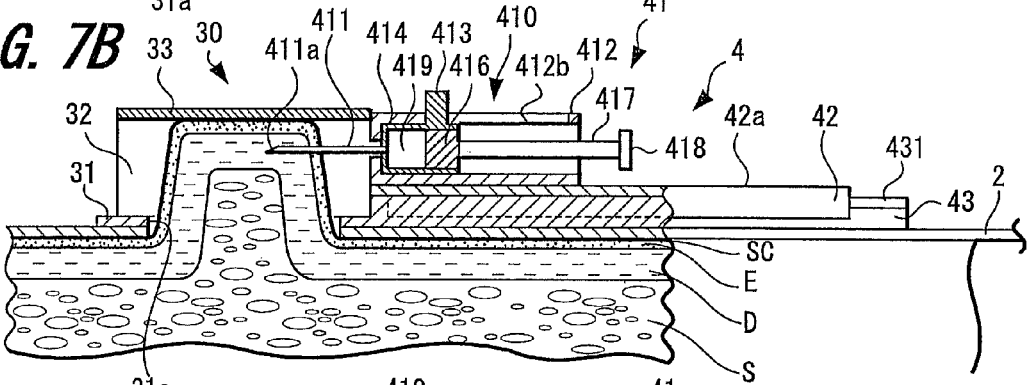

Next, after visually confirming that the skin raised from the opening portion has been raised to a position sufficiently higher than the position of the needlepoint 411a of the piercing needle 411, the gripping portion 413 integrated with the inner tube 414 is gripped and slid toward the distal end along the guiding hole 412b formed in the outer tube 412. Thereby the inner tube 414 is slid inside the outer tube 412, so that the piercing needle 411 provided to the inner tube 414 is pierced into the raised skin. In other words, the piercing needle 411 fixed to the inner tube 414 is inserted from the insertion hole 412c into the site of piercing, so that the needlepoint 411a of the piercing needle 411 is pierced through the epidermis E including the stratum corneum SC into the dermis D substantially in parallel to the dermis D as shown in FIG. 7(b).

Figure 7C:
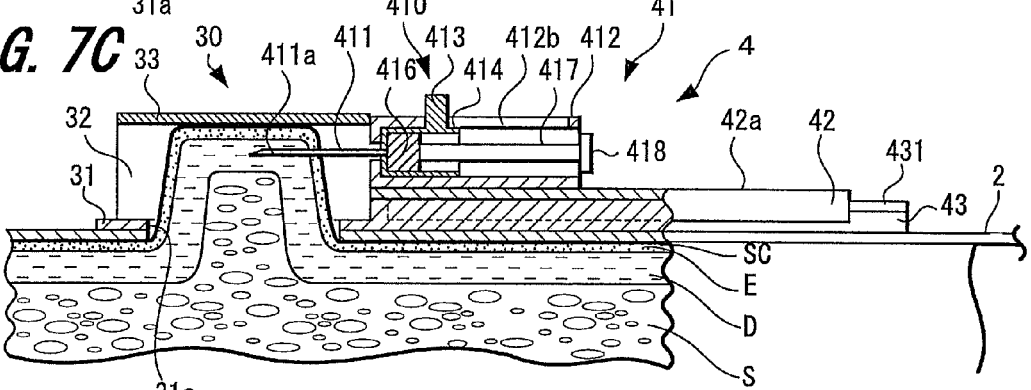

Next, the plunger 417 is operated by pressing the flange 418 with a finger or the like to move the gasket 416 toward the distal end. Thereby, as shown in FIG. 7(c), the liquid housed in the liquid chamber 419 is injected into the dermis D through the needlepoint 411a of the piercing needle 411.

After the liquid is injected into the dermis D, the gripping portion 413 is gripped and slid toward the proximal end along the guiding hole 412b, the piercing needle 411 is pulled out from the raised skin, and the piercing needle 411 is housed in the outer tube 412.

Figure 7D:
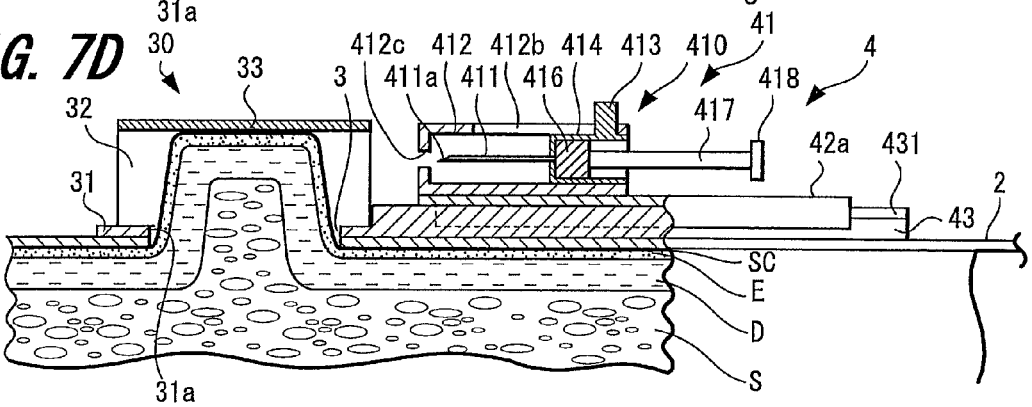

In this state, the mounting member 42 with the injector 41 fixed thereto is slid toward the proximal end so that the piercing tool becomes the state shown in FIG. 7(d), and finally the engaging projection 2a and the engaging hole 2c are disengaged from each other to detach the piercing tool 1 from the body surface F.

With the piercing tool according to the present embodiment, the piercing needle 411 is pierced into the skin in the state where the piercing tool 1 is reliably fixed to the body by the belt 2, so that the needlepoint 411a can reliably reach the predetermined region. Consequently, the medical solution or the like can be reliably injected into the predetermined region.

Figure 9:
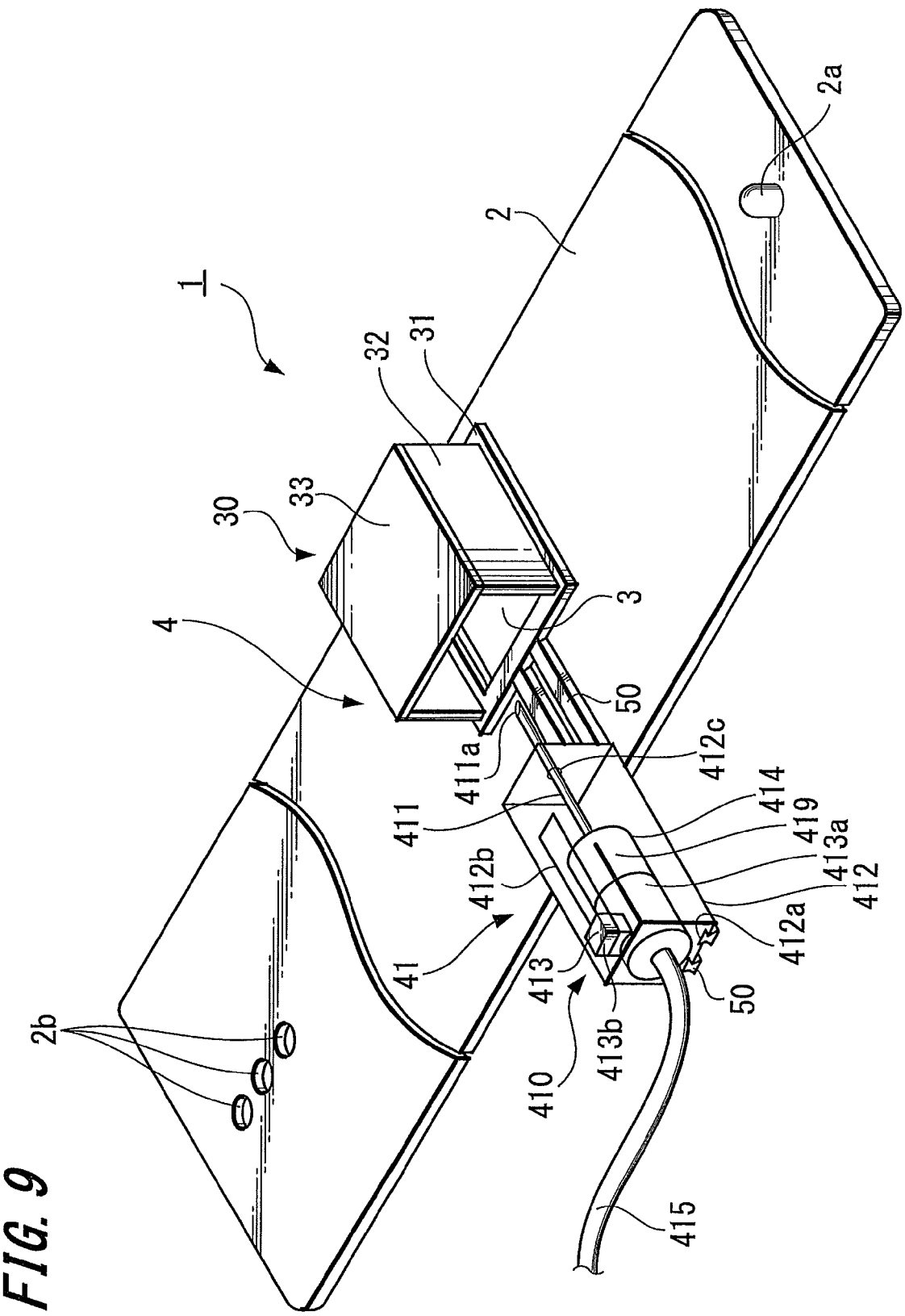
FIG. 9 is a perspective view showing a piercing tool according to a third embodiment of the present invention.
Figure 10:
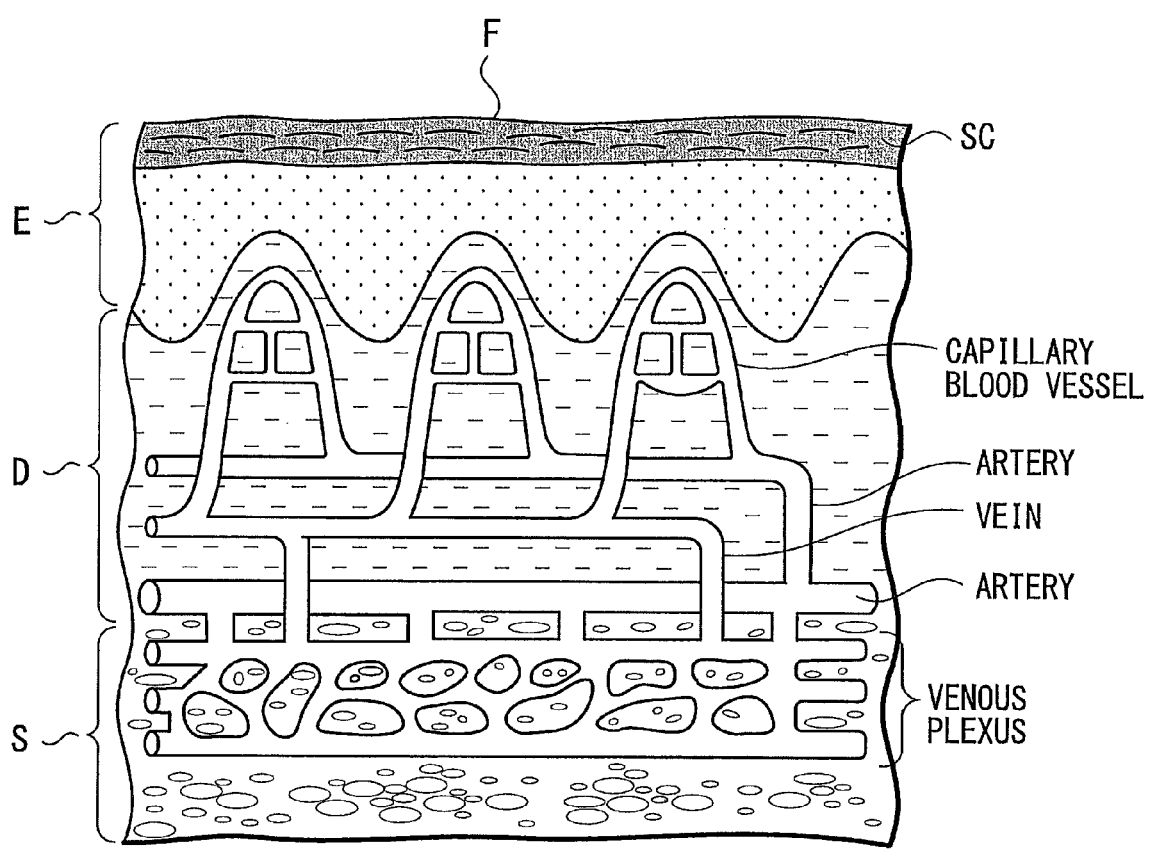
FIG. 10 is a cross sectional view showing a general skin structure.

FIG. 9 is a perspective view showing a piercing tool according to a third embodiment of the present invention.

As shown in FIG. 9, a piercing tool 1, which is a first embodiment of the piercing tool of the present invention, includes a belt-like fixing member 2 for fixing the piercing tool to the body of a user, an opening portion provided in the central portion of the belt 2 and having an opening 3 for upwardly raising skin, a piercing needle moving means 4 for movably holding a piercing needle 411, and the like. The belt has the same configuration as that of the piercing tool according to the first embodiment.

The opening portion for raising skin is formed in a central portion of the belt 2. The rectangular shaped opening 3 is formed in the opening portion. The opening 3 is formed so that the longitudinal direction thereof becomes perpendicular to the longitudinal direction of the belt 2. Further, the opening 3 is formed at a position displaced from the central line of the longitudinal direction of the belt 2 to one side edge of the belt.

A regulating member 30 for adjusting the condition of the skin raised from the opening is provided around the opening 3. The regulating member 30 has the same configuration as that of the piercing tool of the first embodiment.

The piercing needle moving means 4 is provided near the central portion of the belt 2 so as to be adjacent to the opening 3. In other words, in the present embodiment, the opening 3 and the piercing needle moving means 4 are arranged along a direction perpendicular to the longitudinal direction of the belt. The piercing needle moving means 4 includes a guide portion configured by two rails 50 provided on the surface of the belt 2 along the direction perpendicular to the longitudinal direction of the belt 2, and an injector 41 having the piercing needle 411. The injector 41 has the same configuration as that of the piercing tool of the first embodiment.

With the piercing tool according to the present embodiment, the injector 41 can be move in a direction perpendicular to the longitudinal direction of the belt 2. Thus, when attaching the piercing tool to the body, even if the piercing tool is attached in a state where the piercing tool is bent in the longitudinal direction of the belt 2, the rails 50, which are arranged in a direction perpendicular to the longitudinal direction of the belt 2, will not be bent. Thus, the user of the piercing tool can smoothly move the injector 41.

It is to be understood that the piercing tool according to the present invention is not limited to the embodiments described above, and various modifications and variations in material, configuration and the like can be made without departing from the scope of the present invention. For example, in the aforesaid embodiments, when piercing the piercing needle 411 into the raised skin, the gripping portion 413 is manually-operated by gripping with the finger, however the present invention is not limited thereto but includes a configuration in which a spring seat is provided at an end of the outer tube 412 opposite to the needlepoint, and a biasing spring is arranged between the spring seat and the base 413a or the inner tube 414, so that the piercing needle 411 is pierced into the raised skin by the biasing force of the biasing spring.

Further, the piercing tool of the aforesaid embodiments may either be a disposable piercing tool designed to be used only once, or have a configuration in which the injector is detachably attached to the belt, the injector being a disposable injector, while the other parts being reusable.

EXPLANATION OF REFERENCE NUMERALS

1 piercing tool
2 belt
3 opening
4 piercing needle moving means
30 regulating member
31 supporting table
32 side plate
33 top plate
41 injector
50 rail (guide)
410 needle holding member
411 piercing needle
411a needlepoint
412 outer tube
412a engaging recess
412b guiding hole
412c insertion hole
413 gripping portion
413a base
413b grip
414 inner tube
415 tube
416 gasket
417 plunger
418 flange
419 liquid chamber
419a flow passage

The invention claimed is:

1. A piercing tool for piercing a piercing needle into a skin, comprising:
   a belt-like flexible fixing member having an opening formed for raising the skin;
   a piercing needle; and
   a piercing needle moving means mounted on the belt-like fixing member for moving the piercing needle toward a side surface of the skin raised from the opening, wherein, by moving the piercing needle moving means toward the side surface of the skin raised from the opening, the piercing needle is moved so as to pierce the skin raised from the opening through the side surface of the raised skin;
   wherein the piercing needle moving means comprises a movable housing holding the piercing needle movably and a guide portion guiding the housing, and by moving the piercing needle moving means first and then the piercing needle toward the side surface of the skin raised from the opening, the piercing needle is moved so as to pierce the skin raised from the opening.

2. The piercing tool according to claim 1, wherein the belt-like fixing member is provided with an adjusting means for adjusting the fixing position of the piercing tool when attaching the piercing tool to a body.

3. The piercing tool according to claim 1, wherein the opening of the belt-like fixing member is provided with a regulating member for regulating the condition of the skin raised from the opening.

4. The piercing tool according to claim 1, wherein the piercing needle moving means is moved in a direction perpendicular to the longitudinal direction of the belt-like fixing member.

5. The piercing tool according to claim 2, wherein the opening of the belt-like fixing member is provided with a regulating member for regulating the condition of the skin raised from the opening.

6. The piercing tool according to claim 1, wherein the housing comprises an outer tube guided by the guide portion and an inner tube having the piercing needle.

7. The piercing tool according to claim 1, wherein the regulating member comprises a top plate provided above the opening so as to face the opening, and the height of the skin raised from the opening is regulated to a predetermined height by the top plate.

8. A piercing tool for piercing a piercing needle into a skin, comprising;
   a belt-like flexible fixing member having an opening formed for raising the skin;
   a piercing needle; and
   a piercing needle moving means mounted on the belt-like fixing member for moving the piercing needle; wherein, by moving the piercing needle moving means, the piercing needle is moved so as to pierce the skin raised from the opening in parallel with a portion of the belt-like fixing member where the opening is formed; wherein the piercing needle moving means comprises a movable housing holding the piercing needle movably and a guide portion guiding the housing, and by moving the piercing needle moving means first and then the piercing needle toward the side surface of the skin raised from the opening, the piercing needle is moved so as to pierce the skin raised from the opening.

* * * * *